US007123822B2

(12) United States Patent
Gisler-Reinhard et al.

(10) Patent No.: US 7,123,822 B2
(45) Date of Patent: Oct. 17, 2006

(54) AIR HEATER

(75) Inventors: Lukas Gisler-Reinhard, Alpnach Dorf (CH); Pius Studer, Lucerne (CH); Leo Wallimann-Durrer, Alpnachstad (CH)

(73) Assignee: Leister Process Technologies, Sarnen (CH)

( * ) Notice: Subject to any disclaimer, the term of this patent is extended or adjusted under 35 U.S.C. 154(b) by 0 days.

(21) Appl. No.: 11/230,079

(22) Filed: Sep. 19, 2005

(65) Prior Publication Data

US 2006/0068622 A1 Mar. 30, 2006

(30) Foreign Application Priority Data

Sep. 29, 2004 (EP) .................................. 04023222

(51) Int. Cl.
*A61N 33/08* (2006.01)
*F26B 17/12* (2006.01)

(52) U.S. Cl. ........................................ 392/379; 34/168

(58) Field of Classification Search ................ 392/379, 392/200, 360, 473, 478, 479; 34/168, 174, 34/176

See application file for complete search history.

(56) References Cited

U.S. PATENT DOCUMENTS 4,337,584 A * 7/1982 Johnson ......................... 34/65
4,471,213 A * 9/1984 Yoshida ....................... 392/379
4,531,308 A * 7/1985 Neilson et al. ............... 34/168
4,914,834 A * 4/1990 Sime ........................... 34/169
5,033,208 A * 7/1991 Ohno et al. ................... 34/168
5,758,017 A * 5/1998 Hudspeth et al. ........... 392/379
6,079,122 A * 6/2000 Rajkovich .................... 34/574
6,374,510 B1 * 4/2002 Geissbuehler et al. ........ 34/232
2002/0108944 A1 8/2002 Wyss et al.

FOREIGN PATENT DOCUMENTS

EP 0 306 765 A1 3/1989
EP 0 456 173 A1 11/1991

OTHER PUBLICATIONS

European Search Report for corresponding Application No. 04023222.5 dated Dec. 20, 2004.

* cited by examiner

*Primary Examiner*—Daniel Robinson
(74) *Attorney, Agent, or Firm*—Renner, Otto, Boisselle & Sklar, LLP

(57) ABSTRACT

An air heater is provided with a connecting case for the power supply and the air to be heated, as well as a heating element attached to the connecting case by means of a carrier. In the connecting housing, the carrier is connected via a plug connection with the connection board for transmitting the heating current. For this purpose, a receptacle angle bracket is provided that can be inserted into the connecting housing and locked in place. The receptacle angle bracket has cylindrical sleeves serving as electrically insulating bushings for the contact pins on the carrier. In order to tap reference voltages for the control device, the contact pins of the plug connection can be connected with the contact tracks of the connection board of the control device by means of rubber-elastic conductive connecting elements. In order to establish the contact, an injection-molded part made of conductive rubber is used that is pressed against the contact points when the connection board is installed in the connecting housing. The air heater is distinguished by its small number of individual components that allow its quick assembly.

11 Claims, 3 Drawing Sheets

AIR HEATER

TECHNICAL FIELD

This invention concerns an air heater with a connecting case for connecting the power supply and the air to be heated, as well as a heating element attached to the connecting case by means of a carrier, and with at least two line voltage contact elements located in the connecting case.

BACKGROUND OF THE INVENTION

Such air heaters are common and are used extensively in industry. Used in many kinds of manufacturing processes, the air heaters heat the air that is supplied either by an external air source (blower) or by a blower that is attached directly to the air heater. The air is passed through a connecting case for the power supply, or it bypasses this case, and is then heated by a heating element.

Such air heaters must be of robust design to handle the generated heat as well as continuous operation. In addition, they should be designed for simple and quick assembly since a great number of such devices are produced in the course of mass production. In the air heater designs known so far, attaching the electrical connections in particular is a significant time-consuming factor during assembly.

From U.S. Pat. No. 5,033,208, a dry-air drying system for drying plastic granulates for plastic injection molding is known. A cylindrical housing contains two double-wall hollow cylinders of different diameters that are coaxial to each other and to the housing of the drying system. Between them, they form a drying chamber for the material to be dried. The walls of the hollow cylinders facing the drying chamber have openings serving as passages for heated air. The innermost hollow cylinder contains an electric heating system that heats the dry air supplied by a blower flanged to the outside of the housing before it enters the drying chamber. The heated air flows through the material to be dried in the drying chamber before entering the outer hollow cylinder from which it is purged by an exhaust air system.

It is common practice to make the electrical connections—especially with regard to their insulation from the housing—by means of flexible individual leads or flexible connection board connectors, where the electrical connection at the contact points is usually made with impulse welding or manual soldering. Making connections in this manner is time-consuming and leads to high assembly costs. In addition, there is a danger that the connection is interrupted by mechanical impacts or vibrations that would render the device inoperable. Another disadvantage of such connections made with leads is their labor-intensive disconnection in case of repairs.

In special applications, electrical connections are made with rubber-elastic electrically conductive connecting elements that do not have the disadvantages described above. Numerous designs of such elastic connecting elements for the electrical connection of components are known, and are being offered as 'conductive rubber element' by many manufacturers. The term 'conductive rubber element' indicates that it is a component with rubber-like characteristics that is electrically conductive, although it may not necessarily be made of rubber. The electrical conductivity of conductive rubber is achieved by adding conductive materials to the insulating base material. Such contact devices have long been used for the electrical connection of LCD displays with the conductors of connector circuit boards (DE 88 08 947 U1).

Difficulties with the use of conductive rubber elements occur whenever the components to be electrically connected are not parallel and/or if their surfaces are not flat. In such cases, specially shaped conductive rubber elements matching the geometry and the spatial orientation of the contact points to be connected are used. However, since such conductive rubber elements also need to have elastic properties, positive positioning, and thus the establishment of precise contact, is problematic because the conductive rubber elements may deform uncontrollably when the necessary contact pressure is generated.

SUMMARY OF THE INVENTION

This invention addresses the problem by proposing an air heater where the design and the arrangement of the connections for transmitting the electric heating current permit a cost-efficient and quick assembly. In addition, it should also permit the easy connection of an appropriate control device.

This problem is solved by the air heater with the characteristics listed in claim 1. Additional advantageous design variants are described in the sub-claims.

The air heater proposed by the invention has a connecting case for connecting the power supply and the air to be heated, as well as a heating element attached to the connecting case by means of a carrier. In the connecting housing, the carrier for transmitting the electrical heating current by means of a plug connection in the shape of contact pins on the carrier body and corresponding contact elements in the connecting housing is connected with a connection board where, for example, the terminals for the power supply are located. For this purpose, on its wall facing the heating element, the connecting housing has at least two insertion openings aligned with the contact pins on the carrier body. The contact pins are held in a receptacle angle bracket in the connecting housing (usually made of metal) and are electrically insulated from the connecting housing.

Preferably, this receptacle angle bracket is inserted in the connecting housing and has at least two cylindrical sleeves that pass through the insertion openings and insulate the contact pins. In principle, additional cylindrical sleeves may be provided for other connections. Besides serving as insulators, the cylindrical sleeves also function as spacers for the carrier during the assembly. In addition, rest elements and at least one attachment element for the connection board are provided. By designing the receptacle angle bracket as an insert, quick assembly becomes possible, while a secure input for the electric heating energy that is appropriately insulated from the connecting housing is provided at the same time. For this purpose, the receptacle angle bracket can preferably be locked into connecting housing.

In an additional advantageous design, in order to tap reference voltages for the control device, the contact pins can be connected to the conductors of the connection board by means of connecting elements made of conductive rubber in order to pass signals to a control device (microprocessor) located on the connection board. Preferably, an appropriately molded conductive rubber element is used to contact and connect the contact surfaces of the connection board and of the contact pins. Here, an insulating base material is filled with conductive metal or plastic particles that enable the conductive rubber to conduct electric currents. By varying the conductive material or its content, the conductive characteristic of the connecting element can be varied. Thus, the control device located on the connection board is able to detect and evaluate the voltage at the contact pins. In addition, the connecting elements can also be used for limiting the current.

In an advantageous design, the elastic connecting element is held in a support shell in the shape of a U-shaped half-shell at the bottom of the receptacle angle bracket. Placing the elastic connecting element in the support shell ensures its precise positioning and provides support so that the connecting element will not deform uncontrollably when the contact pressure is applied.

By means of the receptacle angle bracket, the connecting housing houses the plug connection consisting of plug contact parts and the corresponding contact pins along with the control device in a closed chamber. In a preferred design, the contact pins are designed as cylindrical sockets arranged on a ring-shaped carrier. The corresponding plug connection parts are designed as pins and attached to individual insulated electrical wires that can be connected via terminal boxes with the connection board of the control device. However, it is also possible to use contact pins on the carrier and sockets on the wires. The carrier has several contact pins of which at least two carry line voltage. The contact pins not carrying line voltage are used for connecting sensors of the control device and/or for grounding metallic parts of the housing. The voltages and signals needed by the control device for control purposes are tapped at the contact pins that can be contacted by the rubber-elastic connecting elements.

Preferably, the connecting element is homogeneous and designed as one piece, and has on its body a recess for accepting the contact pins. The geometry and dimensions of the recess match those of the contact pin; preferably, it is a bore whose inner circumference is slightly smaller than the outer circumference of the contact pin. When the contact pin enters the bore of the connecting element, it expands the bore which causes the connecting element to make positive contact, under pressure, with the surface of the contact pin.

In a further advantageous design, on its side facing the connection board, the connecting element has a pressure element for contacting the contact tracks of the connection board. The pressure element protrudes from the body of the connecting element, is of cylindrical shape, and is molded as part of the body of the connecting element. The pressure element may also have a different shape, or be composed of several individual pressure elements. Preferably, contacting the contact tracks is accomplished by pressing the connection board against the connecting elements—located in the receptacle angle bracket—that are penetrated by the contact pins. By locking the connection board in position on the receptacle angle bracket, the connecting element is compressed and the contact pressure is maintained.

In another advantageous design, on its side facing away from the connecting housing, the carrier has additional socket elements for plugging in the connection contacts of an electric heating element that are arranged in a circle. The socket elements for the heating element are electrically connected with the contact pins of the carrier. Preferably, the contact pins on the carrier are arranged in a row that is parallel to the bottom of the connecting housing and of the receptacle angle bracket. This makes it possible to arrange the connecting elements in the connecting housing in one plane so that only one design variant of the connecting element is needed.

Below, the invention is explained in detail with reference to a design variant shown in the drawings.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

Figure 1:
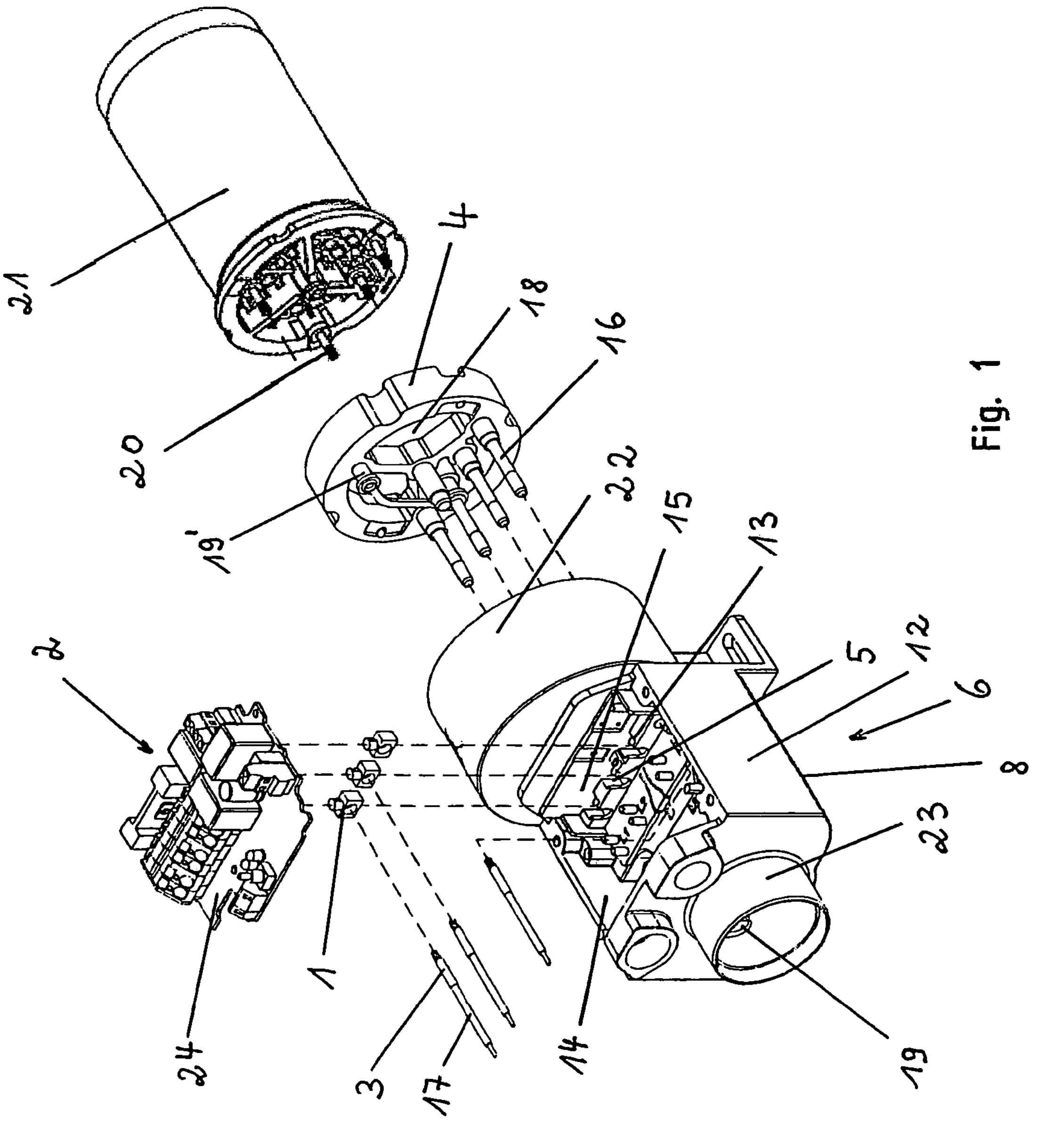
FIG. 1 shows a perspective view of an exploded drawing of an air heater as proposed by the invention.
Figure 3:
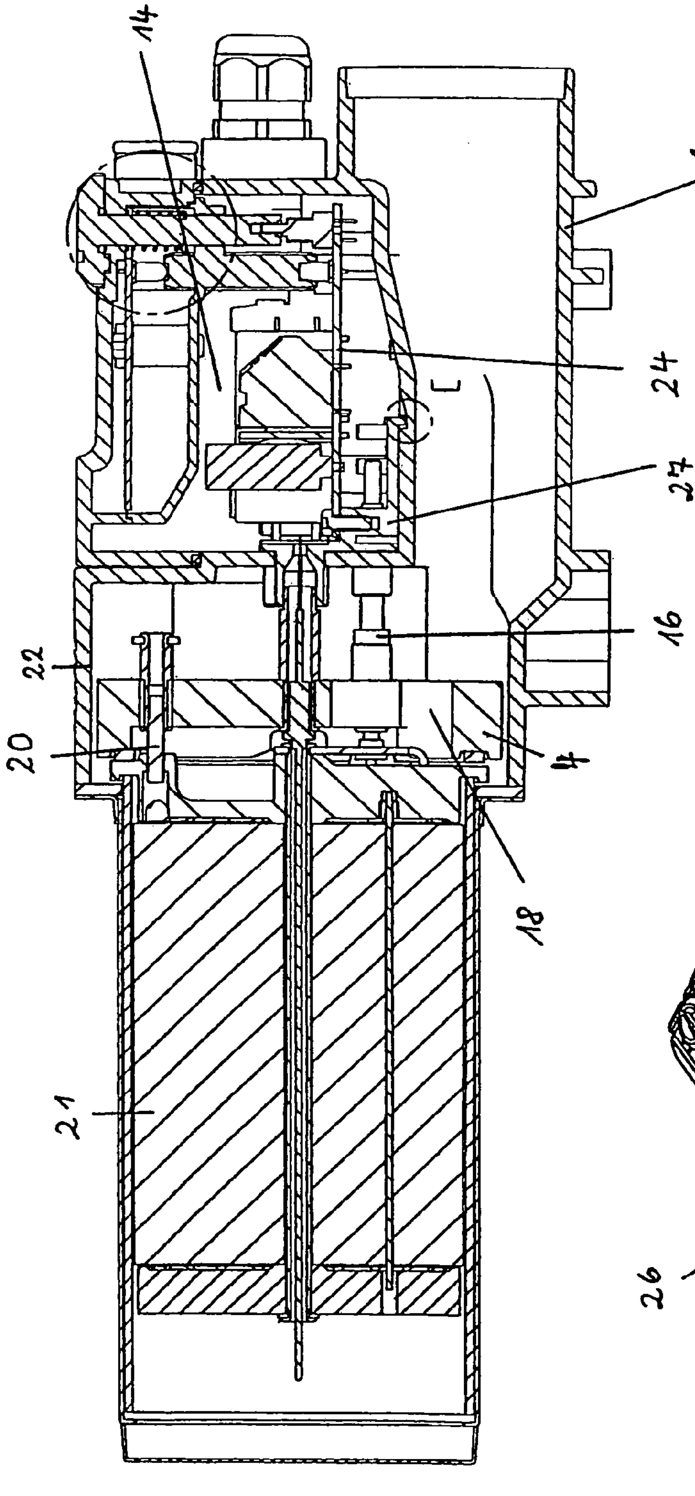
FIG. 3 shows a longitudinal section through the air heater proposed by the invention.

For the sake of clarity, the arrangement of the parts in assembled condition is shown in an exploded view in FIG. 1. Below, the assembled condition as shown by the sectional view in FIG. 3, is described in detail.

The connecting housing 6 shown in FIG. 1, serving to accept a line voltage plug connection 3, 16 and an electrical control device 2, is equipped with electrically conductive flexible connecting elements 1 for making electrical contact with the contact tracks that are connected with electrical components and are located on the connection board 24, and with the contact pins 16 of the plug connection 3, 16. Contacting and connecting the contact surfaces of the connection board 24 and of the contact pins 16 is accomplished by means of a rubber-elastic electrically conductive connecting element 1. The connecting element 1 is held in a U-shaped support shell 5 at the bottom of the receptacle angle bracket 27 inserted into the connecting housing 6 that ensures its precise positioning and support.

In the receptacle angle bracket 27, the connecting housing 6 houses the contact parts 3 and the corresponding contact pins 16 in a closed chamber 14. The contact pins 16 are designed as cylindrical contact sockets and are located on a ring-shaped carrier 4. The plug contact pieces 3 are attached to electrical wires 17 that are connected with the connection board 24 of the control device 2. The contact carrier 4 has four contact pins 16, with at least two of them carrying line voltage. The control device 2 contacts the contact pins 16 via three rubber-elastic connecting elements 1.

The connecting element 1 is homogeneous and of one piece, and has a bore 11 that accepts the contact pins 16. The contact pin 16 enters the bore 11 of the connecting element 1, making positive contact under pressure with the surface of the contact pin 16.

On its side facing the connection board 24, the connecting element 1 has a pressure element 9 for contacting the contact paths of the connection board 24. The pressure element 9 protrudes from the body 10 of the connecting element 1, is of cylindrical shape, and is molded as part of the body 10 of the connecting element 1.

The connecting housing 6 consists of three pieces, i.e. a housing body 12, a receptacle angle bracket 27, and a housing cover (not shown). The housing body 12 has an air duct 19 for carrying compressed air; at the ends of the air duct 19, two connecting pieces 22, 23 are molded as part of the housing body 12. The connecting pieces 22, 23 are designed as inlet piece 23 and outlet piece 22, are of round shape and have different sizes. The outlet piece 22 accepts the ring-shaped carrier 4 that is equipped with air passages 18 for the compressed air. Contact between the rubber-elastic connecting elements 1 and the contact pins 16 is established when the carrier 4 is inserted into the outlet piece 22 of the connecting housing 6. In the area of the outlet piece 22, the housing wall 15 of the housing body 12 and of the receptacle angle bracket 27 have openings 13 that are aligned with the contact pins 16, and through which the contact pins 16 enter the chamber 14 of the housing body 12.

On its side facing away from the connecting housing, the carrier 4 has additional socket elements 19' for plugging in the connection contacts 20, arranged in a circle, of an electric heating element 21. The socket elements 19' for the heating element 21 are electrically connected with the contact pins 16 of the carrier 4. The contact pins 16 on the carrier 4 are arranged in a row that is parallel to the bottom 8 of the connecting housing 6 and of the receptacle angle bracket 27. The connecting elements 1 in the connecting housing 6 are arranged in one plane that is aligned with the corresponding connection parts 16 arranged in a row.

Figure 2:
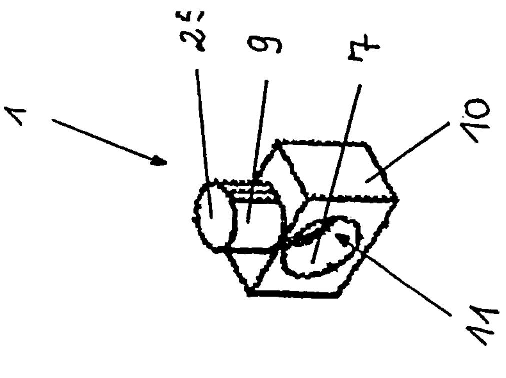
FIG. 2 shows a perspective view of the connecting element according to FIG. 1.

The connecting element 1 as proposed by the invention, shown in an enlarged view in FIG. 2, has the purpose of connecting and establishing electrical contact between the contact pin 16 and the contact tracks of the connection board 24. The connecting element 1 has a cube-shaped body 10 and a cylindrical top piece 9. The cube-shaped body 10 is penetrated by the bore 7. The face surface 25 of the top piece 9 contacts the contact tracks of the connection board 24, and the internal surface 7 of the bore 11 contacts the connecting pins 16.

Figure 4:
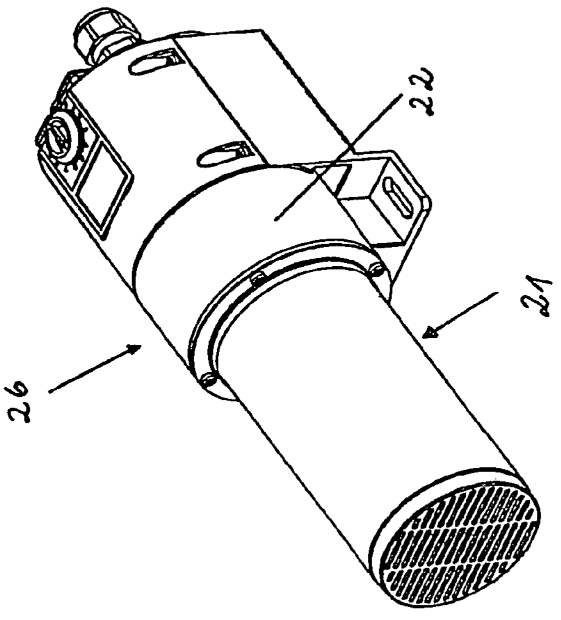
FIG. 4 shows the perspective view of an assembled air heater according to FIG. 3.

FIGS. 3 and 4 show the fully assembled air heater in a cross-section and in a perspective view.

Figure 5:
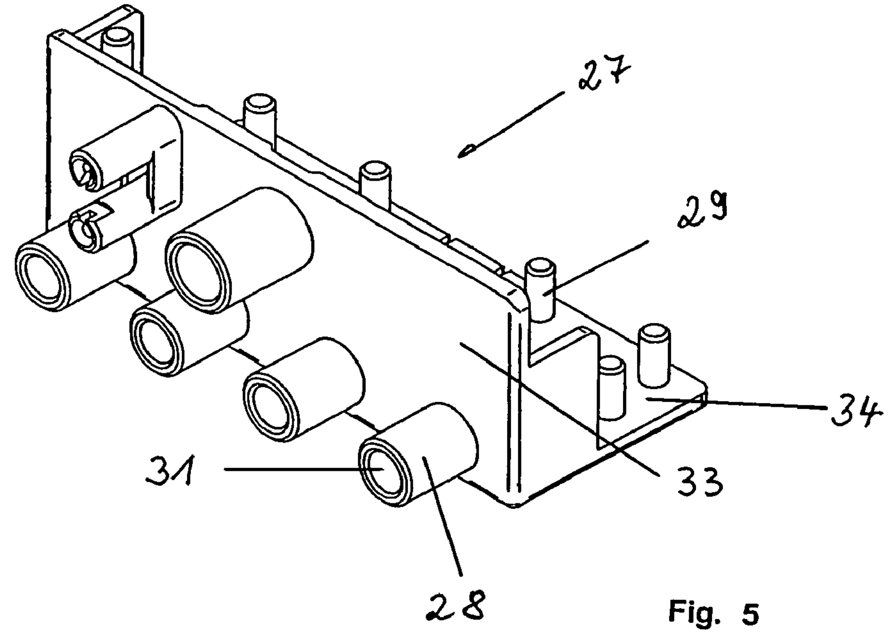
FIG. 5 shows a perspective view of the receptacle angle bracket according to FIG. 1, viewed from the carrier side.
Figure 6:
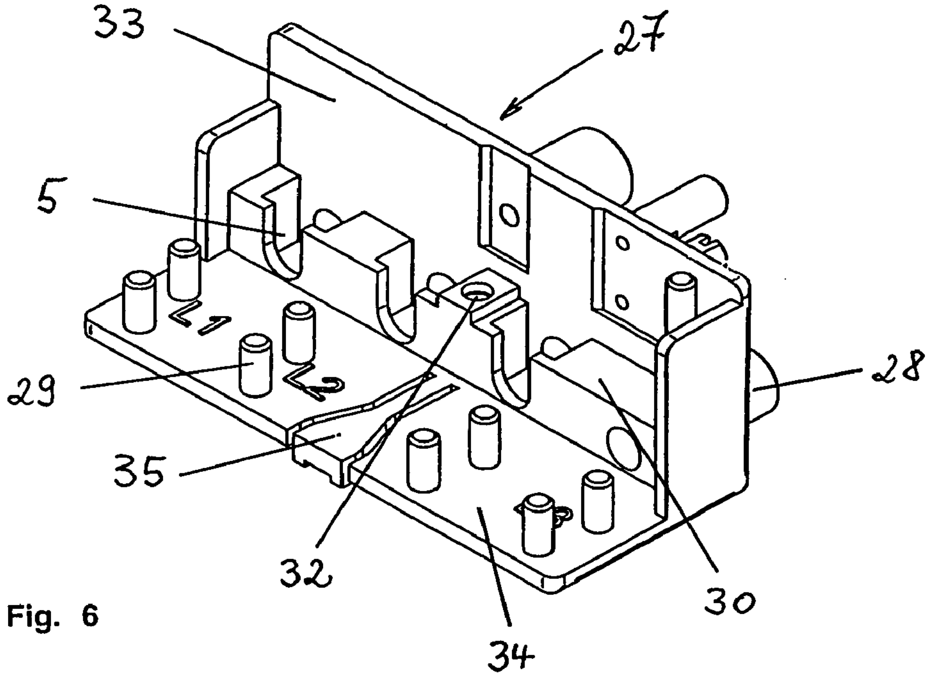
FIG. 6 shows a perspective view of the receptacle angle bracket according to FIG. 5, viewed from the connection side.

FIGS. 5 and 6 show a detail of the receptacle angle bracket 27 in a perspective view. Four cylindrical sleeves 28 with openings 31 through which the contact pins 16 can be inserted are molded as parts of the wall 33 facing the carrier 4. The cylindrical sleeves 28 insulate the connecting pins 16 from the connecting housing 6 and also serve as spacers for the carrier 4 relative to the housing wall 15. The receptacle angle bracket 27 contains rest elements 30 for the connection board 24 (not shown).

They are designed to form the support wall 30 in the area of the support shells 5. In addition, three U-shaped support shells 5 for holding the connecting elements 1 are molded into the bottom 34 of the receptacle angle bracket 27; between two support shells 5, a bore 32 is provided into which a bolt (not shown) for attaching the connection board 24 can be screwed. At its bottom 34, the receptacle angle bracket 27 has a locking element 35 for locking it into the connecting housing 6. This allows the receptacle angle bracket to be inserted and locked in position quickly and easily. The cylindrical sleeves 29 serve as lateral contact protection.

The invention claimed is:

1. An air heater with a connecting case for connecting the power supply and the air to be heated, as well as a heating element attached to the connecting case by means of a carrier, and with at least two line voltage contact elements located in the connecting case, wherein on its wall facing the heating element, the connecting housing has at least two openings through which contact pins can be inserted;

the contact pins are located on the carrier and are aligned with the openings in the housing wall; and the contact pins are held in a receptacle angle bracket of the connecting housing, are electrically insulated from the connecting housing, and are connected with a connection board by means of plug contact elements.

2. The air heater according to claim 1, wherein the receptacle angle bracket can be inserted into the connecting housing and has cylindrical sleeves that pass through the insertion openings and insulate the contact pins, and rest elements and at least one attachment element for the connection board are provided.

3. The air heater according to claim 2, wherein the receptacle angle bracket can be locked into the connecting housing.

4. The air heater according to claim 1, wherein the contact pins are arranged in a row on the carrier.

5. The air heater according to claim 1, wherein, on the side facing the contact pins, the carrier has plug elements that pass through the contact carrier and into which the connection contacts of the electric heating element can be plugged.

6. The air heater according to claim 5, wherein the plug elements on the carrier are electrically connected with the contact pins.

7. The air heater according to claim 1, wherein the carrier is ring-shaped and has air ducts as passages for compressed air.

8. The air heater according to claim 1, wherein, by means of a rubber-elastic connecting element located in a preferably U-shaped support shell of the receptacle angle bracket, at least one contact pin is connected with electrical contact tracks of the connection board for the purpose of transmitting signals to a control device installed on the connection board.

9. The air heater according to claim 8, wherein the connecting element is a homogeneous one-piece molded part made of conductive rubber containing metal or graphite and includes contact elements for contacting the electrical contact tracks of the connection board as well as the contact pins.

10. The air heater according to claim 9, wherein the electrical connection of the connecting element with the contact tracks of the connection board is established through the compression of the connecting element when the connection board is attached to the connecting housing.

11. The air heater according to claim 8, wherein the electrical connection of the connecting element with the contact tracks of the connection board is established through the compression of the connecting element when the connection board is attached to the connecting housing.

* * * * *